United States Patent
Salmon et al.

(10) Patent No.: US 10,360,994 B2
(45) Date of Patent: Jul. 23, 2019

(54) METHOD OF QUANTIFYING HYDROCARBON FORMATION AND RETENTION IN A SOURCE ROCK

(71) Applicant: IFP ENERGIES NOUVELLES, Rueil-Malmaison (FR)

(72) Inventors: Elodie Salmon, Paris (FR); Francois Lorant, Thiais (FR); Francoise Behar, Paris (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 197 days.

(21) Appl. No.: 14/876,399

(22) Filed: Oct. 6, 2015

(65) Prior Publication Data

US 2016/0098543 A1    Apr. 7, 2016

Related U.S. Application Data

(62) Division of application No. 11/833,456, filed on Aug. 3, 2007, now abandoned.

(30) Foreign Application Priority Data

Aug. 4, 2006 (FR) ..................... 06 07148

(51) Int. Cl.
    *E21B 49/00* (2006.01)
    *G01N 33/24* (2006.01)
    *G16C 10/00* (2019.01)
    *G01V 99/00* (2009.01)

(52) U.S. Cl.
    CPC .............. *G16C 10/00* (2019.02); *E21B 49/00* (2013.01); *G01N 33/241* (2013.01); *G01V 99/00* (2013.01); *G01V 99/005* (2013.01); *G01V 2210/661* (2013.01)

(58) Field of Classification Search
    None
    See application file for complete search history.

(56) References Cited

PUBLICATIONS

Xiao. Reviews in Mineralogy and Geochemistry, 2001, v. 42,1, p. 383-436.*
Duin et al. J. Phys. Chem. A, vol. 105, No. 41, 2001, 9396-9409.*

* cited by examiner

*Primary Examiner* — Michael L Borin
(74) *Attorney, Agent, or Firm* — Fitch, Even, Tabin & Flannery LLP (57) ABSTRACT

The method according to the invention allows modelling of oil and the retention phenomenon in the source rock. Organic matter characterization experiments are used to establish the molecular model (MM) of the initial sample. The thermal cracking reaction of this molecular model is reproduced by dynamic molecular simulation computations with a reactive force field and validated by comparison with experimental data. The reaction mechanism permits a kinetic study by variation of the temperature parameter. The successive phase equilibrium assessments at various progress stages of the cracking reaction allow following the physicochemical evolution of the thermal maturation of the organic sample. The free hydrocarbons are not retained in the solid residue can be quantified throughout numerical modelling of the sample maturation.

20 Claims, 5 Drawing Sheets

METHOD OF QUANTIFYING HYDROCARBON FORMATION AND RETENTION IN A SOURCE ROCK

CROSS-REFERENCE TO RELATED APPLICATION

This application is a divisional application of U.S. patent application Ser. No. 11/833,456, filed Aug. 3, 2007, the contents of which are incorporated herein by reference.

BACKGROUND OF THE INVENTION

Field of the Invention

The present invention relates to a method of quantifying hydrocarbon formation and retention within a macromolecular chemical system.

Description of the Prior Art

The following documents, mentioned in the description hereafter, illustrate the state of the art:

Behar F., Vandenbroucke M., Tang Y., Marquis F., Espitalié J., 1997. Thermal Cracking of Kerogen in Open and Closed Systems: Determination of Kinetic Parameters and Stoichiometric Coefficients for Oil and Gas Generation. Org. Geochem., 26, 5-6, 321-339.

Burnham, A. K. and Braun, R. L., 1989. Development of Detailed Model of Petroleum Formation, Destruction, and Expulsion from Lacustrine and Marine Source Rocks. Advances in Organic Geochemisrty, 16, 1-3, 27-39.

Burnham, A. K. and Braun, R. L., 1990. Mathematical Model of Oil Generation, Degradation, and Expulsion. Energy and Fuel, 4, 132-146.

Faulon, J. L., Prediction Elucidation and Molecular Modeling. Algorithms and Applications in Geochemistry, Ph. D. Thesis, Edited by Ecole des Mines, Paris, 1991.

Faulon, J. L., Stochastic Generator of Chemical Structure (4) Building Polymeric Systems with Specified Properties, J. Comput. Chem., 2001, 22, 580-590.

Freund, H., Walters, C. C., Kelemen, S. R., Siskin, M., Curry, D. J., Xiao, Y., Olmstead, W. N., Gorbaty, M. L., Bence, A. E., 2005. Predicting Oil and Gas Compositional Yields via Chemical Structure-Chemical Yield Modeling (CS-CYM). Organic Geochemistry: Challenges for the 21st Century (Vol. 1), 22 IMOG Seville, Spain, 66-67.

Hatcher, P. G., 1988. Dipolar-Dephasing 13C Studies of Decomposed Wood and Coalified Xylem Tissue: Evidence for Chemical Structural Changes Associated with Defunctionalization of Lignin Structual Units During Coalification. Energy & Fuels 2, 48-58.

Pepper, A. S., 1991. Estimating the Petroleum Expulsion Behaviour of Source Rocks: A Novel Quantitative Approach. In Petroleum Migration (Edited by England W. A. and Feed A. J.), Geological Society, Special Publication. 59, pp. 9-31.

Pepper, A. S., Corvi, P. J., 1995. Simple Kinetic Models of Petroleum Formation. PartIII: Modelling and Open system. Marin and Petroleum Geology, 12, 4, 417-452.

Pepper, A. S., Dodd, T. A., 1995. Simple Models of Petroleum Formation. Part II: Oil to GAS cracking. Mar. Petrol. Geol., 12, 321-340.

Ritter, U., 2003. Fractionation of Petroleum During Expulsion fromKerogen. Journal of Geochemical Exploration 0.78-79, 417-420.

Ritter, U., 2003. Solubility of Petroleum Compounds inKerogen: Implications for Petroleum Expulsion. Organic Geochemistry 0.34, 319-326.

Tissot, B. 1969. Revue Inst. Fr. Pétrole, 24(4), 470-501.

Ungerer, P., 1989. State of the Art of Research in Kinetic Modelling of Oil Formation andExplusion. In Advances in Organic Goechemistry, Organic Geochemistry. 16, 1-3, 1-25.

Van Duin A. C. T, Siddharth D., Lorant F., Goddard III W. A. -2001. ReaxFF: A Reactive Force Field forHydrocarbons. J. Phys. Chem. A, 0.105, 9396-9409.

The insoluble organic material of the source rock, also referred to as kerogen, is a mixture of bio-organic macromolecules (notably biogeopolymers) having aliphatic and aromatic chemical structures that evolve in the course of geologic times with the temperature and the pressure. Thermal maturation of the kerogen in the source rock occurs through the agency of two main phenomena:

the first one is thermal cracking of the organic matter at the origin of hydrocarbons; it takes place naturally in sedimentary basins, generally at a temperature ranging between 80° C. and 200° C., and a pressure ranging from 200 to 1000 bar, the second one is the physicochemical evolution of the petroleum products within the source rock that explains the retention and expulsion of hydrocarbons from the source rock.

These two phenomena develop within the same context and they are juxtaposed.

In basin modelling, it is important to be able to simultaneously calibrate the amounts of hydrocarbons formed and the amounts of "free" hydrocarbons that can be expelled from the source rock and migrate to the reservoir. The process of hydrocarbon retention in kerogen is a mechanism that controls the free hydrocarbons/expelled hydrocarbons ratio. If the retention of hydrocarbons is considered to predominantly occurs in the organic matter of the source rock, this retention depends on the composition of the fluids generated, on the retention capacities of the kerogen and on the volume ratio of the solid organic matter to the liquid hydrocarbons. It is thus directly linked with the physicochemical nature of the kerogen and with the conversion ratio (Pepper, 1991).

Kerogen cracking and retention of the products from this reaction being interdependent phenomena that evolve with the thermal maturation of kerogen, it appears necessary to develop a fine analysis of the cracking reaction coupled with the retention of the products formed in the kerogen in order to be able to estimate the hydrocarbons retained in the kerogen and the hydrocarbons available for storage in reservoirs.

There are known hydrocarbon quantification models that account for either the thermal cracking reaction, or the hydrocarbon retention phenomenon, but rarely of both phenomena simultaneously:

empirical and mechanistic cracking models are used to quantify the hydrocarbons formed in the source rock, models of hydrocarbon retention in the source rock try to explain the segregation of the hydrocarbons when they are expelled from the source rock.

Thermal Cracking Models

Two cracking reaction modelling methods are provided in the literature: empirical models and mechanistic models.

Empirical models are based on experiments to establish the global stoichiometric equations that account for the mass balances observed.

These stoichiometric equations are coupled with hydrocarbon formation velocity laws, they correspond to a series of simultaneous, independent and competitive reactions and they were developed assuming that the global evolution of the petroleum potential of a kerogen under maturation is an irreversible kinetic process (Pepper and Dodd, 1995). The kinetic (E: activation energy, A: frequency factor) and stoichiometric (Xi: relative contribution of reaction i) parameters have to be calibrated individually because the source rocks do not generate hydrocarbons at the same rate. Artificial maturation experiments are therefore carried out in the laboratory under controlled thermal conditions. These experiments are performed on kerogens or source rocks and they can be of different natures. By numerical inversion of the laboratory data, it is possible to calculate the kinetic and stoichiometric parameters. These parameters, obtained at high temperature (300° C.-600° C.) over short times (some minutes to some days) are then assumed to be extrapolatable for lower temperatures than those of the experimental conditions such as those imposed by the geothermal gradients.

This method is currently the only means allowing providing information on the formation of hydrocarbons compatible with basin models. However, this procedure is based on many approximations. In fact, Behar et al.'s work of 1997 showed that the differences in the experimental conditions of the pyrolyses carried out (open or closed medium, in the presence or absence of water or of mineral matrix, or according to the grain size of the sample) leads to a kinetic parameters lag and therefore to an uncertainty in the estimation of the oil window. Similarly, extrapolation of the kinetic parameters at low temperature involves the nature of the cracking mechanism does not significantly develop as a function of temperature.

Mechanistic models are not based on stoichiometric equations but on elementary (radical) reactions to simulate the thermal degradation of complex macromolecules and to reproduce the distribution of the hydrocarbons formed (Freund et al., 2005). Elaboration of these models starts by modelling the initial macromolecule. This modelling is constrained by experimental data relative to the structural properties of the sample. It is based on the distribution of the functional groups in the molecule for establishing the probable structure thereof. Once the initial macromolecule is defined, elementary reactions are applied to the structure so as to simulate the formation of the thermal degradation products. Each elementary reaction has its own kinetic properties, valid whatever the temperature scale. It is thus possible to simulate thermal maturation both under laboratory conditions and under geologic conditions.

The advantage of this approach is that it minimizes the uncertainty on the reaction velocities extrapolated to the geologic conditions. On the other hand, the complexity of these models makes elaboration of the reaction mechanism difficult. Finally, and above all, the very large number of reactions in these models is incompatible with current basin simulators.

Retention Models

Physical models have been provided in order to estimate the proportion of expelled hydrocarbons as a function of the kerogen conversion rate. Ungerer's expulsion model (1989) sets a threshold corresponding to a conversion rate for which the hydrocarbons formed in the source rock are expelled. In this connection, Pepper (1991) considers correlating "the petroleum expulsion efficiency" (PPE) with the initial petroleum potential of the source rocks considered. These models reproduce more or less accurately (according to the source rock type) the quality of the hydrocarbons of the reservoir. They consider the source rock in two states only, before and after expulsion of the hydrocarbons, without taking into account the qualitative evolution of the source rock or the expulsion kinematics.

Later, Ritter (2003) provided a retention model based on the solubility of the hydrocarbons in kerogen. He established an empirical relation between the swelling ratio and the Hildebrand solubility parameter, for each type of organic matter. This relation defines a retention ratio for each group of compounds. Finally, this model confirms the fractionation sequence observed in nature, except for branched aliphatic hydrocarbons. The polymer solubility theory and this model thus do not totally explain the hydrocarbon composition differences between source rock extracts and reservoir oils, observed in petroleum systems. Similarly, this model does not explain the great accumulation of aliphatic hydrocarbons in coals. This model has two limitations: the first one is that the values of the swelling ratio are filed according to their chemical class but they are not normalized. Thus, the model does not respect the mass conservation principle. This generates too high retention thresholds and the sum of the compositions is above 100%. The second drawback is due to the fact that the swelling phenomenon involves swelling of the organic matrix. Now, there is little chance that this swelling occurs in rocks subjected to high overpressures.

In conclusion, the expulsion and retention models provided to date involve possible mechanisms and they are developed with more or less assumptions, which leads to more or less realistic approaches. In fact, the structure of kerogen and the nature of the effluents vary with the source rock maturity, therefore thermal cracking and expulsion are indissociable processes.

The method according to the invention allows quantification of the formation and the retention of hydrocarbons in a source rock from a new type of simulation. This simulation type is based on a dynamic molecular modelling technique coupled with a reactive force field. As in the case of mechanistic models, this approach requires as the starting point a "molecular" representation of the structure of the kerogen. The method according to the invention does not require writing hundreds of a priori reactions: the reaction mechanism is not an input datum, it becomes a result of the dynamic simulation. As in the case of radical mechanisms, this new technique is applicable in any thermal regime.

SUMMARY OF THE INVENTION

The invention relates to a method of quantifying the formation and the retention of hydrocarbons within a macromolecular chemical system, comprising construction of a molecular model of the system by means of experimental characterizations of a sample of the system, and comprising:

- defining a thermal maturation reaction mechanism for a macromolecular chemical system by subjecting the molecular model to a molecular dynamic simulation associated with a reactive force field;

quantifying the free hydrocarbons formed throughout the thermal maturation of the macromolecular system by:

a) determining a physicochemical evolution of the molecular mixture defined by the reaction mechanism, by calculating phase equilibria, directly from the molecular dynamic simulation; and b) determining the thermal decomposition kinetics of the macromolecular chemical system by kinetic study from said reaction mechanism.

The present invention comprises a method of modelling the thermal reactivity of macromolecular chemical systems whose molecular structure is unknown or not well known.

In particular, it can be used within the context of basin modelling where the method allows parametrization of the proportion of hydrocarbons formed and possibly retained in the organic matrix of the source rock.

In the description hereafter, what is referred to as "macromolecular chemical system" or "macromolecular system" is a system consisting of at least one organic macromolecule, for example the organic matter of the source rock.

The "reaction mechanism" is understood to be all of the chemical reactions describing the thermal maturation of each macromolecule. A reaction mechanism is associated with a set of quantitative and qualitative data that characterize the reagents, the products and the velocities of the chemical reactions.

A "force field" is a set of parametrized equations that describe the various contributions to the total potential energy of a chemical system (notably Van der Waals, Coulomb, torsional energies).

In the method according to the invention, the molecular model and the reaction mechanism are advantageously validated by comparison of the results from the reactive molecular dynamic simulation with experimental measurements of the thermal maturation of the macromolecular chemical system.

Determination of the phase equilibria is preferably performed by calculating at any time the total energy of each molecule subjected to the force field, then by successive assessments in order to quantify the hydrocarbon retention in the macromolecular chemical system.

The kinetic study is preferably carried out by varying the temperature of the reaction mechanism.

In an embodiment, the macromolecular chemical system represents the organic matter of a source rock of a petroleum reservoir.

The invention also relates to a method of simulating the genesis of a sedimentary basin, wherein the formation and the retention of hydrocarbons within a source rock containing kerogen are modelled, and wherein the following stages are carried out:
defining by means of experimental characterizations a molecular model of the kerogen of the source rock;
defining a reaction mechanism by subjecting the molecular model to a molecular dynamic simulation associated with a reactive force field;
quantifying the evolution of the kerogen to heavy products and hydrocarbons, by carrying out a kinetic study of the thermal decomposition of the kerogen from said reaction mechanism;
quantifying the hydrocarbon retention within the source rock by carrying out assessments on the fractions linked to the organic matrix of the source rock and on the free fractions from the phase equilibria determined by molecular dynamic simulation; and
using as the input data in a basin simulator the amounts of hydrocarbons formed and the amounts of hydrocarbons that are not retained in the source rock, that can be expelled from the source rock and migrate to a petroleum reservoir.

BRIEF DESCRIPTION OF THE DRAWINGS

Other features and advantages of the method according to the invention will be clear from reading the description hereafter of a non limitative embodiment example, with reference to the accompanying figures wherein.

DETAILED DESCRIPTION

The method according to the invention numerically models the thermal maturation of the organic matter of the source rock or of any other macromolecular system, and the retention of the products from this reaction in the residual organic matrix, and to possibly extrapolate the results to the basin scale.

Figure 1:
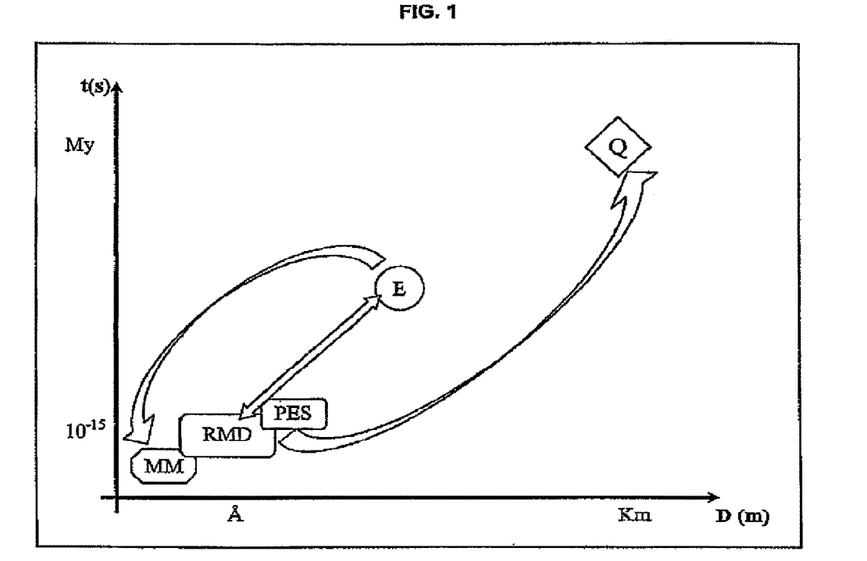
FIG. 1 shows the principle of the method according to the various space and time scales of the phenomena modelled.

FIG. 1 shows the principle of the method as a function of the various space scales (D(m): Distance in meter) and time scales (t(s): time in second). The initial kerogen (or any other macromolecular structure) sample (E) is experimentally characterized, which allows determination of a molecular model of the structure (MM (Å, $10^{-15}$s)). This molecular model is the input datum of the dynamic simulations coupled with a reactive force field (RMD (Å, $10^{-15}$s)). These simulations model the thermal cracking reaction of the molecular model under the given conditions, and they are validated by comparison with the experimental thermal maturation data. At several stages of the simulated reaction, phase equilibrium calculations (PES (µm, $10^{-15}$s)) are carried out in order to establish a physicochemical assessment of the reaction medium. The free hydrocarbons and those retained in the solid residue are estimated on the molecular scale from all of these calculations, then extrapolated to the geologic conditions (Q (Km, Ma)).

Figure 2:
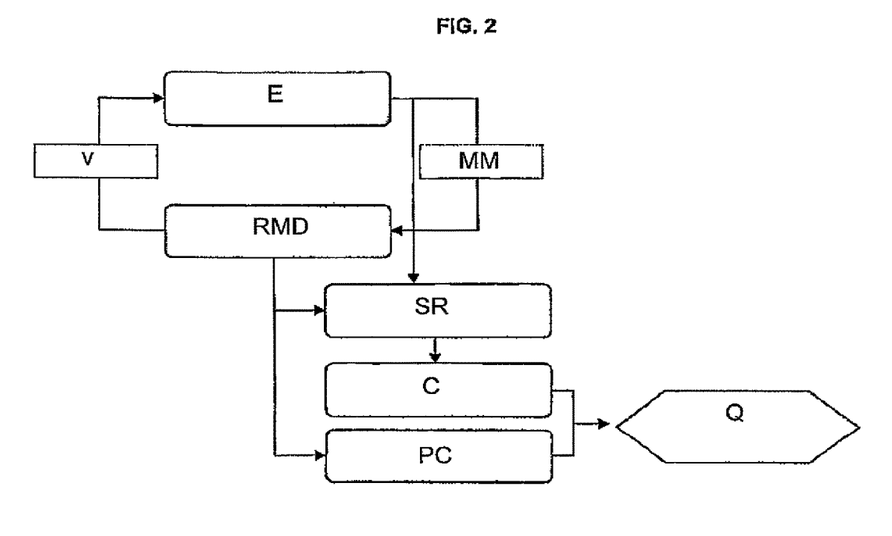
FIG. 2 illustrates the sequence of the stages of the method for reaching evaluation of the hydrocarbons formed and retained in the source rock.

The method can be broken down into three major stages:
1-Determination of the nature and of the molecular structure of the macromolecular chemical system (kerogen for example)
2-Reactive dynamic molecular simulation
3-Thermodynamic study and kinetic study These stages are diagrammatically shown in FIG. 2; from laboratory data on sample (E), a molecular model (MM) of the sample is established and introduced in a reactive dynamic simulation (RMD). The results of the reactive dynamic simulation are validated (V) by comparison with the experimental data. The reactive dynamic simulation (RMD) allows construction of a reaction mechanism (SR) and description of the physicochemical evolution of the retention (PC) from the phase equilibria determination. From the reaction mechanism, the thermal decomposition reaction kinetics is determined, notably by thermal cracking (C). Coupling the kinetic study and the physicochemical study allows quantification of the hydrocarbons produced and the "free" hydrocarbons (Q).

First Stage: Determination of the Molecular Structure and of the Nature of the Organic Matter—Elaboration of a Molecular Model The first stage of this method determines the structure and the nature of the macromolecular system (notably organic matter of the source rock) that will be used as initial data for modelling the thermal maturation reaction. For example, many organic matter characterization techniques, such as elementary analysis (AE), Fourier transform infrared spectroscopy (FT-IR), nuclear magnetic resonance spectroscopy (NMR) and X-ray diffraction (DRX), can be used to quantify the various functions and to know the spatial distribution of the molecular structure. Similarly, indirect characterization techniques such as the study of pyrolysis products are also an efficient means of determining macromolecular structures. Using molecular models such as Signature (random macromolecular generator, Faulon, 1991 and 2001) associated with the experimental characterization data can allow obtaining a more realistic macromolecular system. The first stage of the method according to the invention allows to establish a molecular model of the macromolecular system.

Second Stage: Reactive Dynamic Molecular Simulation

The cracking reaction of the molecular model of the macromolecular system is reproduced by dynamic molecular simulation calculations coupled with a reactive force field (RMD). These simulations are compared with experimental thermal maturation data (quantitative data (conversion, mass balance, elementary analysis . . . ) and qualitative data (product characterization (by gas chromatography coupled with a mass spectrometer GC-MS, magnetic resonance NMR, Fourier transform infrared spectroscopy FT-IR, X-ray diffraction DRX . . . ) from pyrolyses in open or closed media, or other thermal maturation experiments depending on the simulation conditions). The similarity between the experimental and numerical results validates both the molecular model of the initial sample and the reaction mechanism provided by the simulation.

Dynamic simulations are three-dimensional molecular modellings allowing representation of a set of molecules in a force field describing the energy status of the medium. In a given volume, a system of molecules having n atoms and m bonds will turn into a system keeping a number n of atoms but evolving towards a number m' (different from or equal to m) of bonds.

Van Duin et al. (2001) provide a reactive force field called "Reaction Force Field" (ReaxFF). This force field is an intermediate approach between the quantum models and the non-reactive force fields.

The two particular features of this field are that its energy function is based on the order of the bonds between atoms, and that there is a continuity between the binding energies and the non-binding energies. The result is a rather complex energy function that incorporates the partial energy contributions allowing to describe the various types of bonds, as well as the cleavages and the formation of bonds:

$$E_{total}=E_{bond}+E_{over}+E_{under}+E_{val}+E_{pen}+E_{tors}+E_{conj}+E_{vdw}+E_{coulomb}$$

with:
$E_{bond}$=binding energy
$E_{under}$=undercoordination energies
$E_{over}$=overcoordination energies
$E_{val}$=valence energy
$E_{pen}$=penalty term (associated with $E_{over}$, $E_{under}$ in the case of allenes)
$E_{tor}$=torsional energy
$E_{conj}$=conjugation energy
$E_{vdw}$=van der Waals energy
$E_{coulomb}$=Coulomb energy A parametrized analytical function relating the energy to the order of the bonds involved corresponds to each energy term. For example, the binding energy between two atoms i and j is written as follows:

$$E_{bond}=-D_e \cdot BO_{ij} \cdot \exp(p_{be,1}(1-BO_{ij}^{Pbe,1}))$$

where $BO_{ij}$ is the order of the bond between i and j, $D_e$ and $D_e$ and $p_{be,1}$ are parameters calibrated for different atom pairs. According to Pauling's principle, the bond order itself depends on the relative distance between the atoms. In the case of pluriatomic systems, calculation of $BO_{ij}$ between two atoms takes account of the atomic environment. Van Duin et al. (2001) developed a calculation mechanism relating the bond orders to the relative positions of the atoms in space while taking account of all of these interactions.

To date, ReaxFF allows carrying out dynamic simulations on systems consisting of at least one of the following atoms: C, H, O, N, S, Si, Pt, Zr, Ni, Au, V, Bi, Ti, Mo. The parameters associated with the different energy terms are calibrated by numerical inversion of both the experimental data (generally reaction enthalpy) and the theoretical data calculated by means of quantum methods.

Concerning the dynamic simulation as such, ReaxFF comes in form of a software including both the force field (in form of an auxiliary file) and the molecular dynamics engine. This engine takes up the basic principles of dynamic simulation wherein the motion of the atoms is described by the Newtonian mechanics in the three-dimensional space:

$$\begin{cases} \vec{F}_i = m_i \frac{d^2 \vec{r}_i(t)}{dt^2} = -\frac{d\vec{E}}{dr_i(t)} \\ \vec{E} = f(BO_{ij}) = f'(r_1, \ldots, r_n) \end{cases}$$

with: $F_i$=force exerted on atom i
$r_i$=trajectory of atom i.

Thus, dynamic simulations with force field ReaxFF allow reproduction of the intra and intermolecular mechanisms of chemical reactions.

Figure 4:
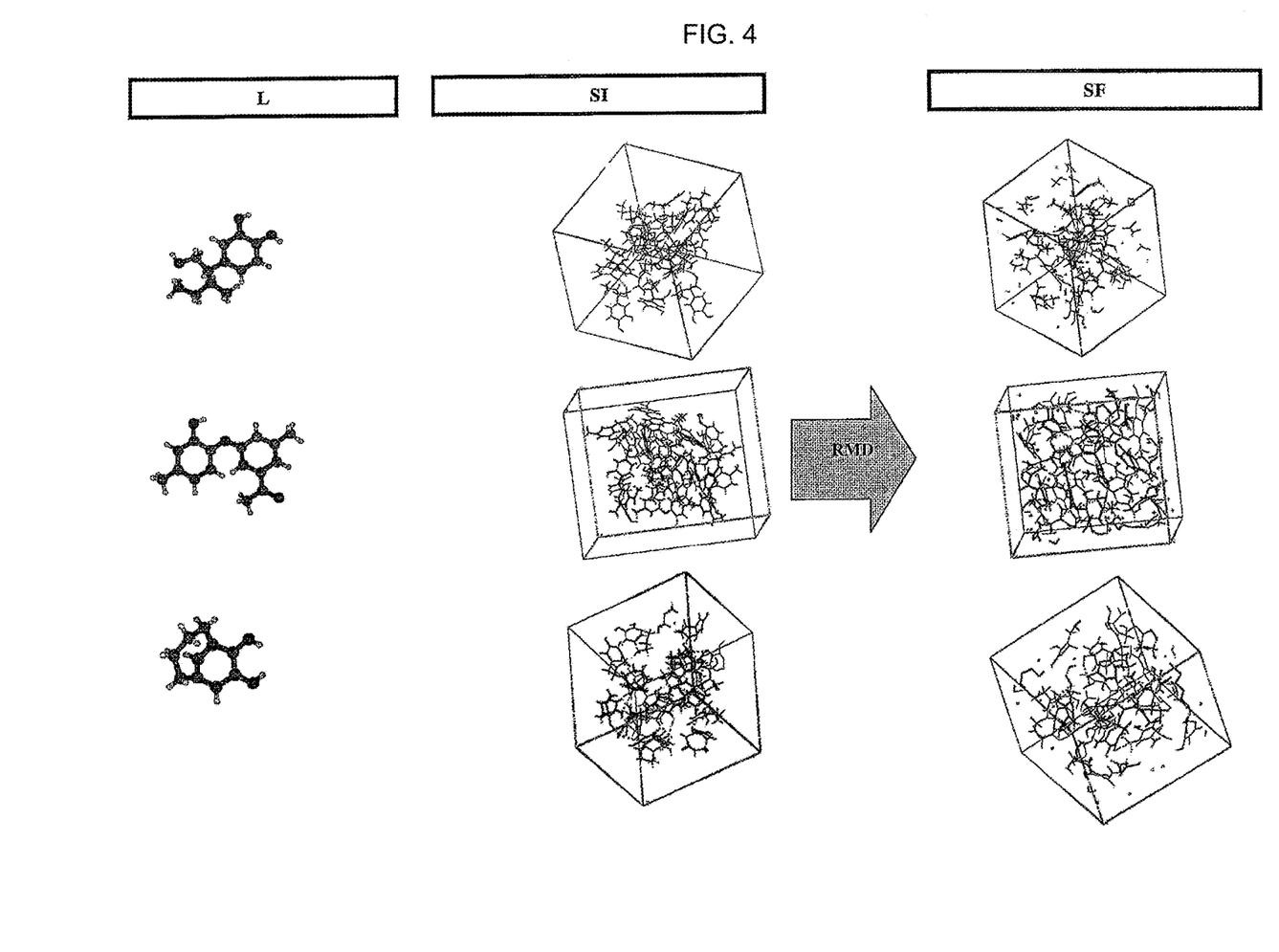
FIG. 4 illustrates the result of the reactive dynamic simulations according to the invention on three molecular models of lignite fragments.

FIG. 4 illustrates the main parameters of the reactive dynamic simulations on three lignite fragments. First (SI), one or more molecules ($N_0$ atoms and $M_0$ atomic bonds) are constructed in three dimensions in a box of predetermined dimensions. It is possible to vary the volume parameters of the box, the pressure and/or temperature parameters during integration of the model as a function of time. A succession of states of the system (SF) evolving as a function of time in the force field ($N_0$ atoms but Mt ($\neq$Mo) bonds) is obtained.

Third and Fourth Stages: Thermodynamic Study and Kinetic Study

The dynamic simulation results allow establishing a reaction mechanism and they can be interpreted or developed according to two approaches:
physicochemical approach of the reaction by studying the phase equilibria: thermodynamic study,
kinetic approach of the decomposition reaction for quantifying the formation of the products predominantly formed or the dissociation of the initial model kerogen: kinetic study.

Physicochemical study (PC): at each time interval, the dynamic simulation calculates the total energy of each molecule of the force field. From these energies, it is possible to sort out the molecules according to their physical state (liquid, solid or gaseous). The physical evolution of each molecule can then be monitored during simulation of the reaction. The successive phase equilibrium assessments (PES) allows following the physicochemical evolution of the thermal maturation of the sample studied. This thermodynamic analysis allows study and qualification of the thermolysis products that are independent of the "residue" (one or more molecules in solid phase and of high molecular mass) of the dependent products.

Kinetic study (C): the kinetic study of the reaction requires dynamic calculations at different temperatures. At each temperature, quantitative assessments of the appearance or disappearance of predominant molecules are established in order to calculate the reaction velocity (k: rate of appearance or of disappearance of a chemical species). From the values of different reaction velocities of each chemical species at the different temperatures, it is then possible to calculate the kinetic parameters (activation energy $E_a$ and pre-exponential factor A) and to deduce therefrom the thermal decomposition kinetics of each molecular species in the temperature range studied.

Finally, from a double study (physicochemical and kinetic) of the mechanisms provided by the dynamic simulations, the free hydrocarbons (liquid and gaseous), not retained in the solid residue, can be quantified throughout the numerical maturation of the sample. They represent, in sedimentary basins, the hydrocarbons likely to be expelled from the source rock (Q) and they can thus be an input parameter for basin simulators.

Example: Study of Lignitic Coal

The Australian brown coal of this example essentially consists of lignite molecules (L). Some characteristics of this coal and of related chemical structures are given in Hatcher's work, 1988.

Definition of the Initial Chemical System: Molecular Model

Figure 3:
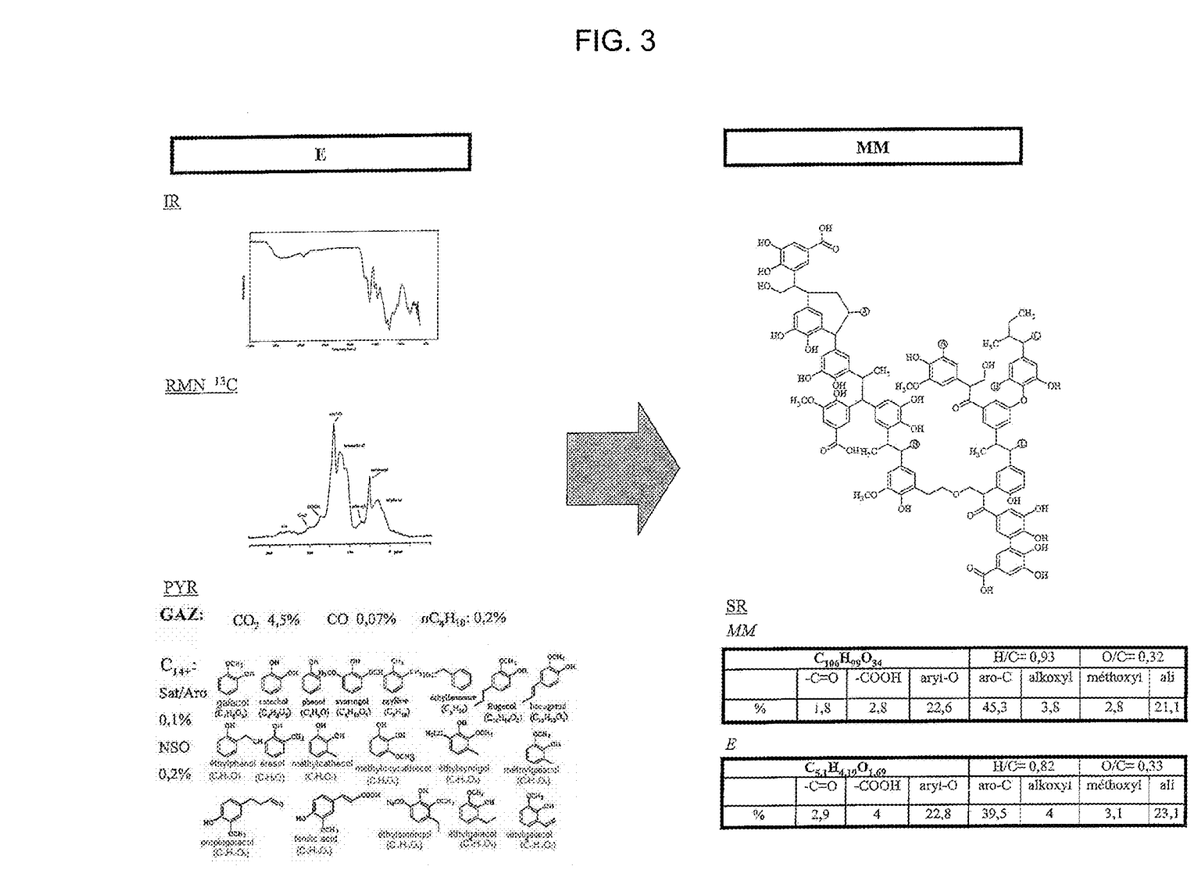
FIG. 3 illustrates the lignite molecular characterization protocol.

First, from experimental organic matter characterization measurements carried out on a sample of this coal (NMR analysis, infrared spectroscopy IR, atomic composition, pyrolyses in closed circuits PYR-FIG. 3), the chemical functions are identified and counted, then, by comparison with the lignite structures provided by Hatcher (Hatcher, 1988), one deduces that the coal can be correctly represented as an agglomerate of a form of lignite that is modelled by a macromolecule of about 250 atoms. In this example, the kerogen model is manually constructed. For more complex kerogens, simulators such as Signature (Faulon 1999, 2001) can be used to randomly organize known units of the structure.

Thermal Reactivity Modelling: Reactive Dynamic Simulation (RMD)

Once the initial chemical system is defined, the thermal reactivity of all or part of the chemical structure deduced in the previous stage is then modelled. A molecular dynamic simulation algorithm associated with a particular force field, called ReaxFF (van Duin et al., 2001), and allowing prediction of, among other things, the thermal cracking of organic matter under given conditions, is therefore used. Examples of such simulations are shown in FIG. 4. In these examples, we have modelled the thermal cracking of three typical fragments of the lignite structure shown in FIG. 3. For each one of the three lignite fragments (L) selected:
Number of units: 15
Volume: 3723.2 Å$^3$
Density: 1.4 kg·L$^{-1}$
Number of units: 17
Volume: 5661.2 Å$^3$
Density<1.4 kg·L$^{-1}$
Number of units: 21
Volume: 4870.9 Å$^3$
Density<1.4 kg·L$^{-1}$ For each fragment, these simulations are carried out as follows:
a volume containing n units of the same fragment is constructed with the algorithm,
after an initialization stage (atom velocities balancing and calculation of the system density at experimental P and T), the reactive dynamic simulations are carried out under different thermal conditions and at constant volume. In FIG. 4, temperature T is above 2000 K. Although the physical duration modelled is finally of the order of some picoseconds, the calculation times can be very long (some hours to some days CPU).

At the end of a computation, in the final systems (SF), the volume contains new molecules from the various thermal decomposition mechanisms that have affected the initial lignite fragments (initial systems SI). The software allows identification of and counting of all of the molecules present in the volume at any time. Fine analysis of these data thus allows both prediction of the composition of the cracking products of the initial fragments and determination of the mechanisms at the origin thereof.

Figure 5:
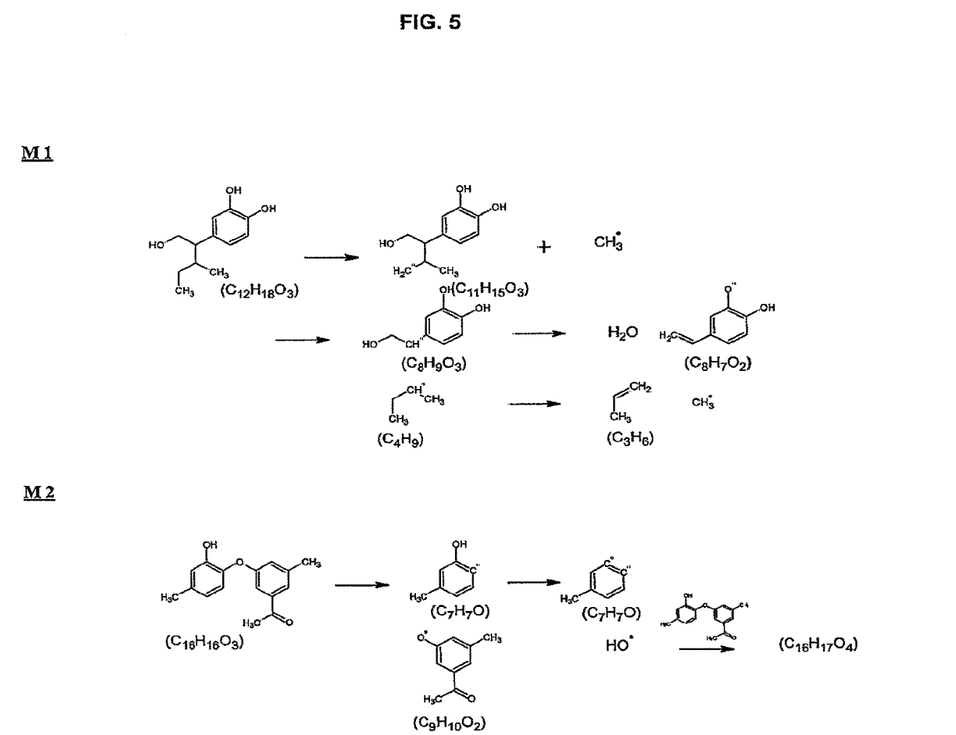
FIG. 5 illustrates the lignite thermolysis mechanisms.

Assessment of the Reactive Dynamic Simulation Results: Achieving a Reaction Mechanism In a third stage, the results of the reactive dynamic simulations are assessed in order to extract therefrom a general coal thermal decomposition mechanism. In the example given, this work shows (FIG. 5) that the major part of the experimentally observed pyrolysis products is obtained by means of two main cracking mechanisms affecting the lignite. These two reactions explain both the formation of water and of methane, through a defunctionalization process (mechanism 1-M1), and the depolymerization in stages (mechanism 2-M2) of the lignite, at the origin of the constituents of the $C_{14+}$ fraction illustrated in FIG. 3.

In conclusion, a general pyrolysis mechanism for the coal studied should have the form as follows:
the lignite undergoes depolymerization in fragments,
the fragments undergo defunctionalizations and give molecules such as molecules of water (H2O), methane (CH4) and other hydrocarbons.

Kinetic Study

In order to quantify the thermolysis of lignite, a kinetic study is carried out from the reaction mechanism predicted by reactive dynamic modelling.

In general terms (Tissot 1969, Braun and Burnham 1989 and 1990, Pepper and Corvi 1995), the primary cracking models correspond to a series of simultaneous reactions, independent and competitive, describing the mass transfer between the source kerogen and the hydrocarbons. A reaction mechanism example is given below. A velocity law of order 1 that depends both on time and on temperature corresponds to each reaction of the mechanism. Thus, the amount m of hydrocarbons formed in the course of time is expressed by:

$$\begin{cases} m = X_{inf} \sum_{i=1}^{N} X_i q_i \\ \frac{dq_i}{dt} = k_i(1-q_i)^n \end{cases} \quad (1)$$

with: $q_i$=conversion ratio of reaction i
$X_i$=relative contribution of reaction i
$X_{inf}$=petroleum potential
$k_i$=velocity constant of reaction i
n=order of the reaction
$X_i$ and $k_i$ obey the following laws:

$$\sum_{i=1}^{N} X_i = 1 \quad (2)$$

$$k_i = A_i \exp\left(-\frac{E_i}{RT}\right) \quad (3)$$

with $A_i$=frequency factor and $E_i$=activation energy for reaction i.

Thermodynamic Study of the Molecules

From the reaction mechanism of the dynamic simulations, it is also possible to sort out the molecules formed according to their molecular weight and to determine their thermodynamic state. Simulators using the Monte Carlo method allow theoretical study of the phase equilibria in a molecular mixture. Using this method or an equivalent method on the molecular mixture (products and reagents of the lignite thermolysis) allows monitoring of the thermodynamic evolution of the reaction with time. This thermodynamic analysis allows studying and quantification of the thermolysis products that are independent of the "residue" (one or more molecules in solid phase and of high molecular mass) of the dependent products.

The potentialities of molecular modelling allow producing complex molecular models (case of kerogen), to predict the thermodynamic properties at equilibrium of these chemical structures, and to calculate parameters involved in the retention, such as viscosity, diffusion, density, phase state, electrostatic charges distribution, binding and repelling forces, to predict the thermal reactivity of these structures according to pressure and temperature, and to determine the chemical nature of the products formed.

The method according to the invention uses a reactive dynamic simulation, which allows prediction of the evolution of the kerogen to heavy products and hydrocarbons, as well as to perform assessments on the fractions linked to the organic matrix and on the free fractions, thus to quantify the retention.

Figure 6:
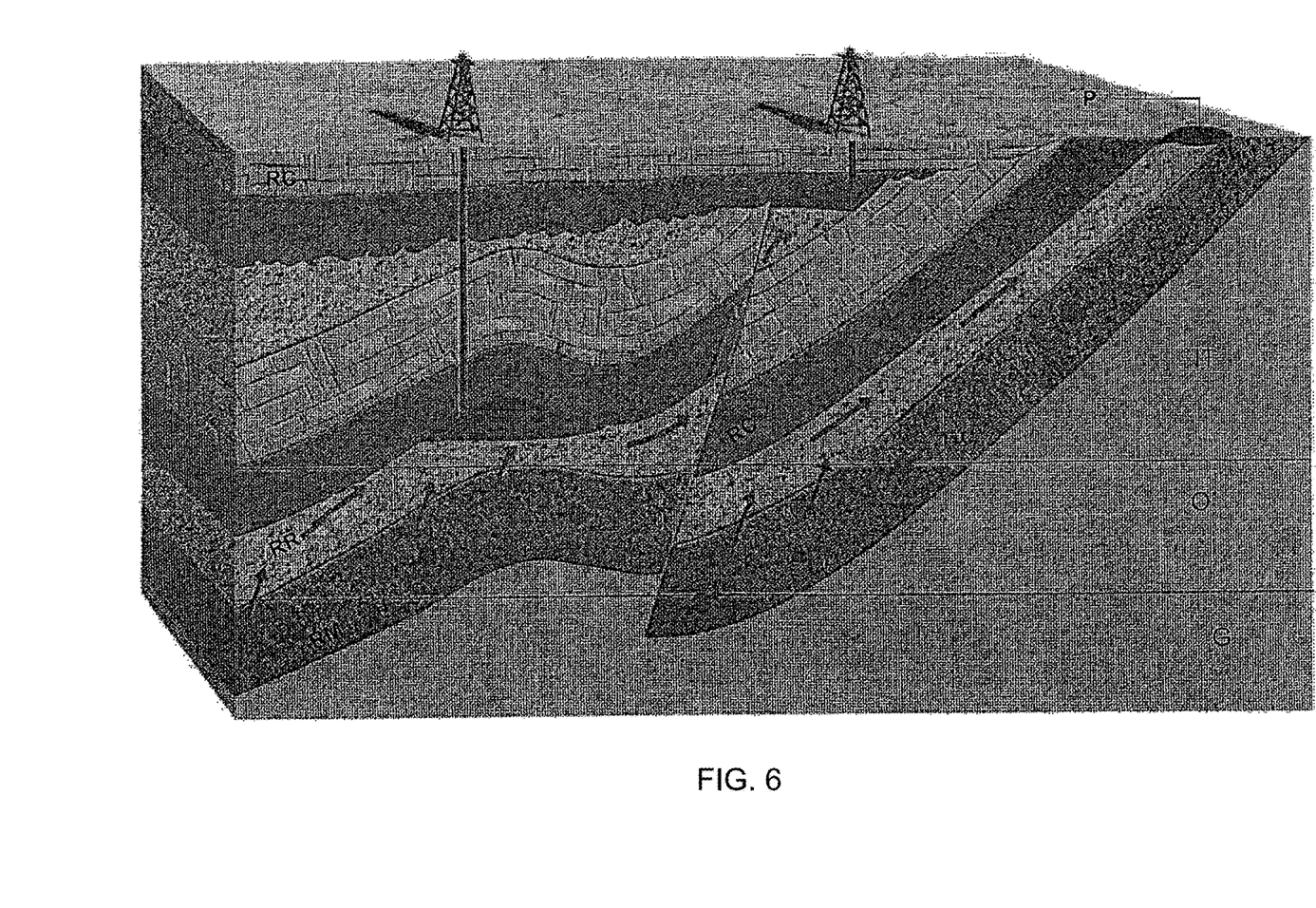
FIG. 6 is a cross-sectional view of an oil development field.

The method for modelling the thermal reactivity of complex chemical systems was applied for quantifying the formation and the retention of hydrocarbons within a complex carbon-containing system such as the organic matter contained in a source rock. FIG. 6 shows an example of an oil exploration system. Zone G represents the gas window (generally temperature above 150° C. and pressure above 53 MPa). Zone O represents the oil window (temperature generally ranging between 80° C. and 150° C., pressure ranging between 24 MPa and 53 MPa). Zone IT is the thermal immaturity zone (temperature below 80° C. and pressure below 24 MPa). The "free" hydrocarbons migrate from the source rock (RM) to the reservoir zone (RR). In the absence of cap rock (RC) at the surface, the petroleum (P) can seep at the surface. Boreholes are drilled through the rock layers to take the crude from the reservoir rock (RR).

This modelling can also find applications in other particular spheres in order to understand and/or quantify a multiscale process that can be simulated through experiment and explained by complex and/or unknown chemical mechanisms. Non limitative examples thereof are the thermal behavior of heavy crudes during steam or air flooding in a reservoir, and hydrocracking of asphaltenes during refining.

We claim:

1. A method of extracting hydrocarbons from boreholes drilled into a petroleum reservoir that are not retained in source rock which simulates a genesis of a sedimentary basin by modelling formation and retention of hydrocarbons within a macromolecular chemical system including the source rock containing kerogen, the method comprising:
   determining structure of the macromolecular chemical system by experimentally characterizing a sample of the macromolecular chemical system used for establishing a molecular model of the macromolecular chemical system;
   using the structure of the macromolecular chemical system as initial data for modeling a thermal maturation reaction with the modeling of the thermal maturation reaction using dynamic molecular simulation calculations coupled with a ReaxFF force field to establish a reaction mechanism; and
   quantifying thermal maturation of the macromolecular system by determining, at stages of a physicochemical evolution of a molecular mixture defined by the reaction mechanism, amounts of hydrocarbons retained in the source rock by calculating phase equilibria directly from the dynamic molecular simulation calculations and by assessing fractions linked to an organic matrix of the source rock and free fractions from the phase equilibria, determining amounts of hydrocarbons formed by thermal decomposition kinetics of the macromolecular chemical system by kinetic study of the reaction mechanism;
   simulating the genesis of the sedimentary basin by using as input data in a basin simulator amounts of hydrocarbons in a petroleum reservoir that have formed in and are not retained in the source rock and are free to migrate to the petroleum reservoir; and
   drilling boreholes into the petroleum reservoir for extracting the hydrocarbons when the simulation of the genesis predicts that migration of extractable hydrocarbons has taken place into the petroleum reservoir.

2. The method as claimed in claim 1, wherein the molecular model and the reaction mechanism are validated by comparison of results from the dynamic molecular calculations with experimental measurements of the thermal maturation of the macromolecular chemical system.

3. The method as claimed in claim 1, wherein the kinetic study is carried out by varying temperature of the reaction mechanism.

4. The method as claimed in claim 2, wherein the kinetic study is carried out by varying temperature of the reaction mechanism.

5. The method as claimed in claim 1, wherein the source rock is in a petroleum reservoir.

6. The method as claimed in claim 2, wherein the source rock is in a petroleum reservoir.

7. The method as claimed in claim 3, wherein the source rock is in a petroleum reservoir.

8. The method as claimed in claim 4, wherein the source rock is in a petroleum reservoir.

9. The method as claimed in claim 2, wherein the kinetic study is carried out by varying temperature of the reaction mechanism.

10. The method as claimed in claim 2, wherein the source rock is in a petroleum reservoir.

11. The method as claimed in claim 3, wherein the source rock is in a petroleum reservoir.

12. The method as claimed in claim 5, wherein the source rock is in a petroleum reservoir.

13. The method as claimed in claim 1, further comprising:
defining a set of molecules in the ReaxFF force field using the dynamic molecular simulation calculations coupled with the ReaxFF reactive force field;
calculating a total energy of each molecular in a set of molecules at a plurality time interval to determine the physicochemical evolution of each molecule in the set of molecules;
calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and
evaluating the physicochemical evolution of each molecule in the set of molecules together with the thermal decomposition kinetics of each molecule in the set of molecules, in order to quantify the free hydrocarbons.

14. The method as claimed in claim 2, further comprising:
defining a set of molecules in the ReaxFF force field using the dynamic molecular simulation calculations coupled with the ReaxFF reactive force field;
calculating a total energy of each molecular in a set of molecules at a plurality time interval to determine the physicochemical evolution of each molecule in the set of molecules;
calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and
evaluating the physicochemical evolution of each molecule in the set of molecules together with the thermal decomposition kinetics of each molecule in the set of molecules, in order to quantify the free hydrocarbons.

15. The method as claimed in claim 3, further comprising:
defining a set of molecules in the ReaxFF force field using the dynamic molecular simulation calculations coupled with the ReaxFF reactive force field;
calculating a total energy of each molecular in a set of molecules at a plurality time interval to determine the physicochemical evolution of each molecule in the set of molecules;
calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and
evaluating the physicochemical evolution of each molecule in the set of molecules together with the thermal decomposition kinetics of each molecule in the set of molecules, in order to quantify the free hydrocarbons.

16. The method as claimed in claim 4, further comprising:
defining a set of molecules in the ReaxFF force field using the dynamic molecular simulation calculations coupled with the ReaxFF reactive force field;
calculating a total energy of each molecular in a set of molecules at a plurality time interval to determine the physicochemical evolution of each molecule in the set of molecules;
calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and
evaluating the physicochemical evolution of each molecule in the set of molecules together with the thermal decomposition kinetics of each molecule in the set of molecules, in order to quantify the free hydrocarbons.

17. The method as claimed in claim 5, further comprising:
defining a set of molecules in the ReaxFF force field using the dynamic molecular simulation calculations coupled with the ReaxFF reactive force field;
calculating a total energy of each molecular in a set of molecules at a plurality time interval to determine the physicochemical evolution of each molecule in the set of molecules;
calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and
evaluating the physicochemical evolution of each molecule in the set of molecules together with the thermal decomposition kinetics of each molecule in the set of molecules, in order to quantify the free hydrocarbons.

18. The method as claimed in claim 6, further comprising:
defining a set of molecules in the ReaxFF force field using the dynamic molecular simulation calculations coupled with the ReaxFF reactive force field;
calculating a total energy of each molecular in a set of molecules at a plurality time interval to determine the physicochemical evolution of each molecule in the set of molecules;
calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and
evaluating the physicochemical evolution of each molecule in the set of molecules together with the thermal decomposition kinetics of each molecule in the set of molecules, in order to quantify the free hydrocarbons.

19. The method as claimed in claim 7, further comprising:
defining a set of molecules in the ReaxFF force field using the dynamic molecular simulation calculations coupled with the ReaxFF reactive force field;
calculating a total energy of each molecular in a set of molecules at a plurality time interval to determine the physicochemical evolution of each molecule in the set of molecules;
calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and
evaluating the physicochemical evolution of each molecule in the set of molecules together with the thermal decomposition kinetics of each molecule in the set of molecules, in order to quantify the free hydrocarbons.

20. The method as claimed in claim 8, further comprising:
defining a set of molecules in the ReaxFF force field using the dynamic molecular simulation calculations coupled with the ReaxFF reactive force field;

calculating a total energy of each molecular in a set of molecules at a plurality time interval to determine the physicochemical evolution of each molecule in the set of molecules;

calculating reaction velocities of each molecule in the set of molecules at difference temperatures, and calculating kinetic parameters for each molecule in the set of molecules from the reaction velocities, in order to determine thermal decomposition kinetics of each molecule in the set of molecules; and evaluating the physicochemical evolution of each molecule in the set of molecules together with the thermal decomposition kinetics of each molecule in the set of molecules, in order to quantify the free hydrocarbons.

* * * * *